United States Patent
Day et al.

(10) Patent No.: US 7,121,829 B2
(45) Date of Patent: Oct. 17, 2006

(54) MOUNT FOR HOLDING AND RELEASING DENTAL IMPLANT COMPONENTS

(75) Inventors: Thomas Day, Carlsbad, CA (US); Jeff Bassett, Vista, CA (US)

(73) Assignee: Zimmer Dental Inc., Carlsbad, CA (US)

(*) Notice: Subject to any disclaimer, the term of this patent is extended or adjusted under 35 U.S.C. 154(b) by 24 days.

(21) Appl. No.: 10/372,364

(22) Filed: Feb. 21, 2003

(65) Prior Publication Data

US 2003/0224326 A1 Dec. 4, 2003

Related U.S. Application Data

(60) Provisional application No. 60/385,801, filed on Jun. 4, 2002.

(51) Int. Cl.
*A61C 3/00* (2006.01)
*A44B 11/25* (2006.01)

(52) U.S. Cl. .............. 433/163; 433/173; 24/129 R

(58) Field of Classification Search ............... 433/163, 433/173, 174; 206/369, 368, 63.5, 306, 379; 24/484, 30.5 S, 129 D, 129 W
See application file for complete search history.

(56) References Cited

U.S. PATENT DOCUMENTS

| | | | | | |
|---|---|---|---|---|---|
| 2,783,515 | A | * | 3/1957 | Tobias ........................ | 24/545 |
| 4,471,512 | A | * | 9/1984 | Thalenfeld .................. | 24/557 |
| 4,901,402 | A | * | 2/1990 | Begemann ................. | 24/129 D |
| 5,182,838 | A | * | 2/1993 | Stenner ..................... | 24/712.7 |
| 5,249,337 | A | * | 10/1993 | Cross et al. .............. | 24/129 R |
| 5,440,788 | A | * | 8/1995 | Boden ....................... | 24/115 H |
| 6,142,296 | A | * | 11/2000 | Klardie et al. ............ | 206/63.5 |
| 6,152,147 | A | * | 11/2000 | Sanchez .................... | 132/324 |
| 6,159,008 | A | * | 12/2000 | Kumar ....................... | 433/163 |
| 6,315,562 | B1 | * | 11/2001 | Kumar ....................... | 433/173 |
| 2003/0054319 | A1 | * | 3/2003 | Gervais et al. ............ | 433/173 |

* cited by examiner

*Primary Examiner*—Todd E. Manahan
(74) *Attorney, Agent, or Firm*—Conley Rose, P.C.

(57) ABSTRACT

A mount for holding and releasing dental implant components. The mount has a generally cylindrical body with a capture formed in the body. The capture includes an opening that is deformable between two positions. In a first position, a dental component is frictionally captured or engaged in the opening. In a second position, the dental component is released or disengaged as the opening deforms.

16 Claims, 3 Drawing Sheets

MOUNT FOR HOLDING AND RELEASING DENTAL IMPLANT COMPONENTS

CROSS-REFERENCE TO RELATED APPLICATIONS

This application claims benefit of priority of U.S. Provisional Application Ser. No. 60/385,801 filed Jun. 4, 2002.

FIELD OF THE INVENTION

The disclosure herein generally relates to implantable dental prostheses and, more particularly, to a mount for holding and releasing dental implant components.

BACKGROUND OF THE INVENTION

A complete product line in implant dentistry consists of hundreds of different dental components. These components include dental implants, abutments, healing components, analogs, copings, and screws, just to name a few. Each of these components is typically available in several different sizes, and each of these sizes is relatively small in length. In fact, most dental components measure only several millimeters in length and width. Because of small size, these components are often pre-assembled to mount or holders. For example, an implant delivery system can include a specialized vial for holding the dental implant and driver mount and mount for holding a cover screw. These components are neatly and systematically assembled in the vial and ready to use during a surgical implantation procedure.

In many instances, the dental components are individually packaged and shipped. A surgeon, for example, may order replacement parts, such as a single healing collar, cover screw, abutment, or the like. In other instances, the components are not pre-assembled and always shipped separately.

Unique challenges arise when dental components are individually packaged and shipped. Since individual parts are so tiny, they can easily become lost. Further, once the part is removed from the packaging, it is very difficult to handle because the hand and fingers are so large compared to the part itself.

Some manufacturers pre-assemble these individual parts in a plastic mount. Specifically, the part is threaded into a threaded bore located in the mount. A threaded attachment between the mount and part, though, has distinct disadvantages. First, a separate tool may be needed to remove the part from the mount. A screwdriver or hex tool, for example, must engage an end of the part in order to unscrew it from the mount. This added step of obtaining a tool and unscrewing the part from the mount is quite time consuming during a surgical procedure. Second, as the part is unthreaded from the mount, small plastic shavings can be forced out of the bore. These shavings can fall on the floor of the operating room or even in the sterile surgical field. Regardless, the generation of unwanted waste in the form of shavings is highly undesired.

Further this mount could be made to cooperate with a dental implant delivery system to deliver for example the cover screw placed on the implant during the healing phase. The mount in some embodiments could be assembled with implant holding vial to create a system form delivering first the implant and then the cover screw.

It therefore would be advantageous to provide an improved mount for holding small dental components. The components could be easily removed from the mount and not generate any unwanted waste during the removal procedure.

SUMMARY OF THE INVENTION

The present invention is directed to a mount for holding and releasing dental implant components. The mount has a generally cylindrical or elliptical body with a capture formed in the body. The capture includes an opening that is moveable between two positions. In a first position, a dental component is frictionally captured or engaged in the opening. Here, the dental component is not free to move from the body of the mount. In a second position, the dental component is released or disengaged from the opening. Here, the dental component is free to move from the body of the mount.

A force imposed on the exterior of the body moves the capture from the first position (an undistorted or capture state) to the second position (a distorted or release state). Specifically, as the mount is distorted with an external force (such as a compressive or tensile force), the body compresses or squeezes together. This compression, in turn, causes the opening in the capture to alter its configuration. In particular, the opening enlarges enough to release the dental component. Once the opening enlarges, the capture no longer frictionally engages the dental component.

One important advantage of the present invention is that the mount holds and releases a dental component and simultaneously generates no waste, such as shavings, debris, or the like. The mount captures (such as frictionally engages) and releases (such as frictionally disengages) the dental component. A threaded engagement between the dental component and mount is not necessary.

As another advantage, a separate tool is not required to engage or disengage a dental component from the mount. As the external surface of the body is squeezed with a hand, the dental component disengages from the mount.

One advantage of the present invention is that the dental component can be released from the mount with action of a single hand. The mount is sized and shaped so it can be placed between the thumb and fingers of one hand. As the thumb and fingers squeeze the body, the capture disengages from the dental component.

Another advantage is that the capture is adapted to engage, capture, and then release a variety of dental components with different sizes and shapes. As compressive forces are applied to the body of the mount, the size and shape of the capture change. The amount of this change depends, in part, on the amount of the compressive force. The capture can be compressed with a relatively larger force to enlarge and then engage and hold larger dental components. Alternatively, the capture can be compressed with a relatively smaller force to enlarge and then engage and hold smaller dental components.

Another advantage of the present invention is that the mount can be made from a pliable or compressable polymeric material. This material resiliently returns to its original shape after a compressive force is removed from the body. As such, the mount can be repeatedly compressed if necessary. In other embodiments the mount could be designed to work to stay deformed after the application of a force.

Other advantages as well will be evident upon reviewing the drawings and reading the detailed description portion.

DETAILED DESCRIPTION

Figure 1:
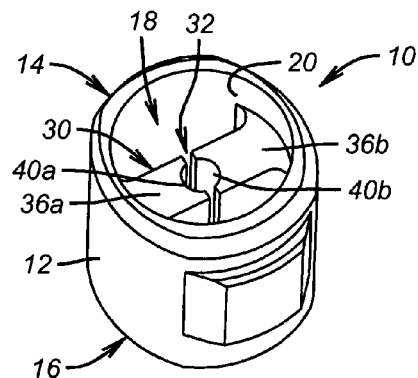
FIG. 1 is a perspective view of a mount for holding dental components according to the invention.
Figure 2:
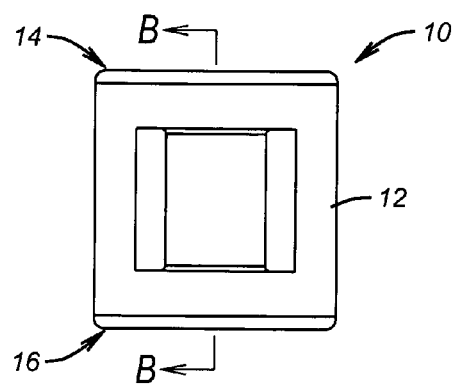
FIG. 2 is a side view of the mount of FIG. 1.
Figure 3:
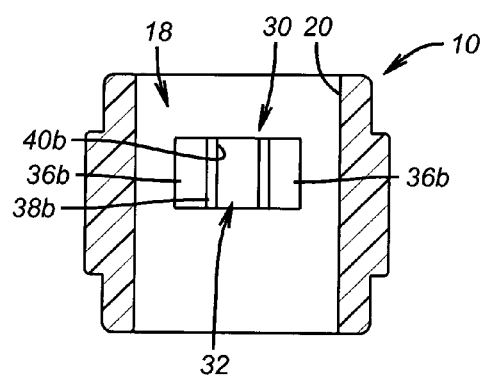
FIG. 3 is a cross sectional view taken through the lines B—B of FIG. 2.
Figure 4:
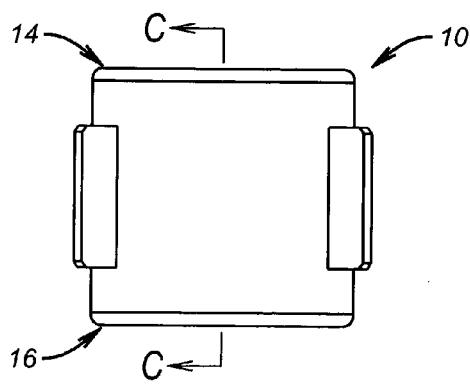
FIG. 4 is another side view of the mount of FIG. 1.
Figure 5:
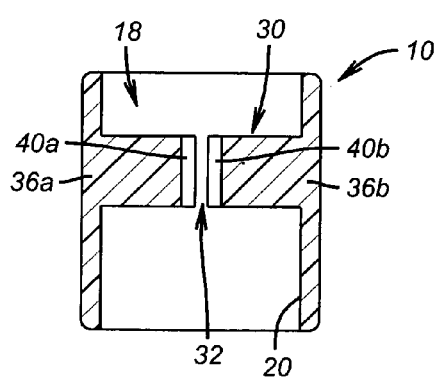
FIG. 5 is a cross sectional view taken through the lines C—C of FIG. 4.

Looking to FIGS. 1–5, mount 10 of the present invention is shown in more detail. The mount generally has a cylindrical body 12 that extends from a proximal end 14 to a distal end 16. Body 12 forms a hollow cylinder with an internal cavity 18 defined along an inside wall 20. Preferably, the proximal and distal ends are open and lead into this cavity. Alternatively, these ends could be provided with removeable lids or ends. Further, the distal end of the body could be permanently closed or sealed with a bottom surface, while the cavity is accessible from the proximal end.

Mount 10 is adapted to hold and then release a dental component. To achieve this function, the mount is provided with a capture 30. The capture is formed inside cavity 18 between the proximal and distal ends. A bore, recess, socket, or opening 32 is formed in the capture. Preferably, this opening is formed generally in the center of cavity 18 and from two oppositely disposed attachment members 36a and 36b that project inwardly from wall 20 in cavity 18. These attachment members have a rectangular shape in cross section and include elongated hemispherical channels or recesses 40a and 40b that project down the entire distal end 38a and 38b of the attachment members. These recesses are oppositely disposed from one another and are spaced apart. The recesses are positioned adjacent each other to form the opening 32. Preferably, this opening is shaped as an elongated bore, such as a cylindrical bore.

Figure 6:
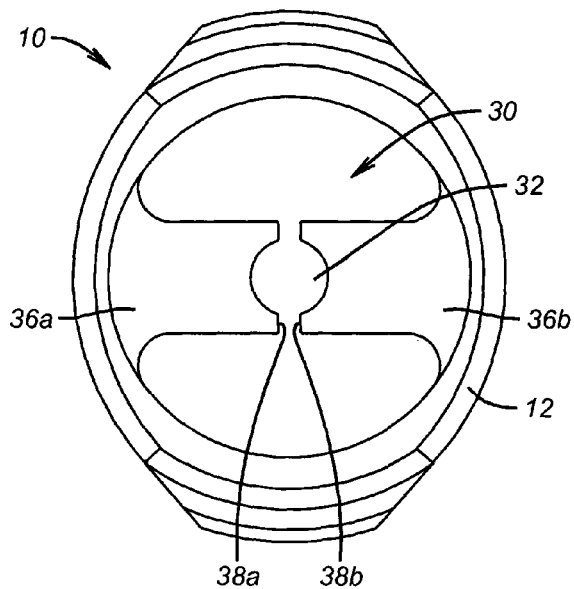
FIG. 6 is a top view of the mount in a non-compressed state.
Figure 7:
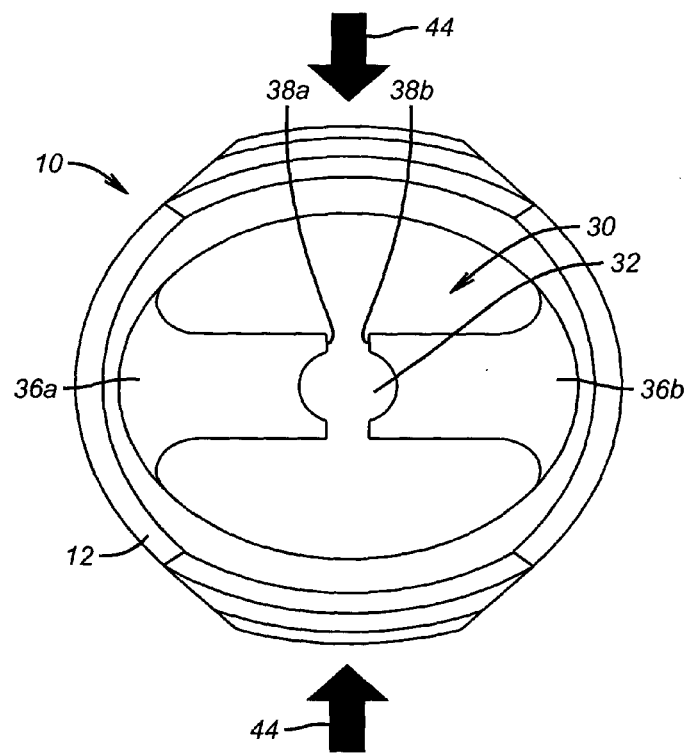
FIG. 7 is a top view of the mount in a compressed state.

Looking also to FIGS. 6 and 7, capture 30 is further discussed. The opening 32 is moveable between two positions. In a first position (shown best in FIG. 6), the opening is in an undistorted state and generally forms a circular shape. In a second position (shown best in FIG. 7), the opening is in a distorted state and generally forms an elliptical or distorted circular shape. As shown in FIG. 7, when a distortive force 44 is applied to the mount 10, the body 12 slightly deforms. In turn, capture 30 deforms. Specifically, opening 32 widens. Body 12 has a more elliptical shape in this distorted or second position. Further, the distance between the distal ends 38a and 38b of attachment members 36a and 36b has increased. After the force 44 is removed from the body 12, the mount may return to its original shape shown in FIG. 6 if it is fabricated from an elastic material Various forces can be applied to the body to distort it and transition it from the undistorted state to the distorted state. The force 44, for example, can be a compressive or squeezing force. Alternatively, this force could be a tensile force or other force applied to the body to distort it.

Figure 8:
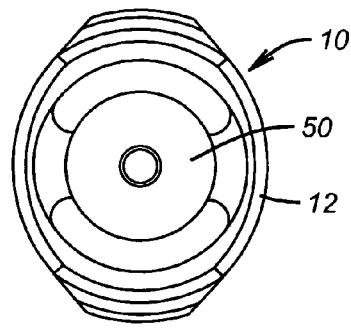
FIG. 8 is a top view of the mount with a dental screw disposed in the body of the mount.
Figure 9:
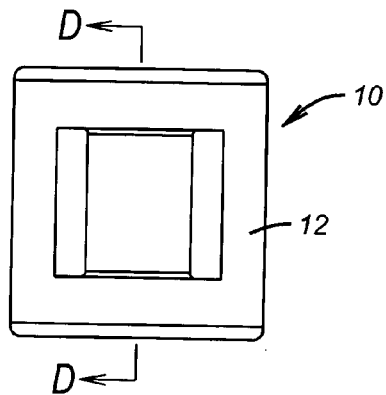
FIG. 9 is a side view of the mount of FIG. 8.
Figure 10:
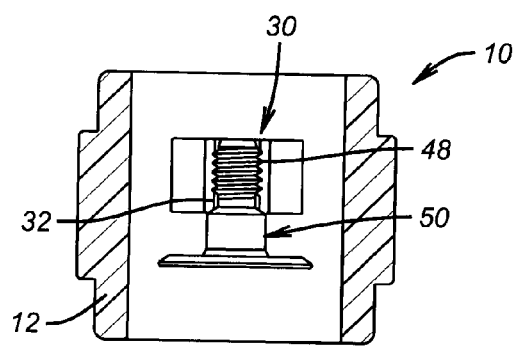
FIG. 10 is a cross sectional view taken through the lines D—D of FIG. 9.

FIGS. 8–10 show a dental component 50 that is frictionally captured or engaged in the opening 32 of capture 30. Here, the dental component is not free to move from the body of the mount. Specifically, opening 32 frictionally engages a shaft or body portion 48 of dental component 50. In this position, mount 10 and accompanying dental component 50 can be moved, packaged, transported, and the like with the dental component securely captured in the body. In order to disengage or remove the dental component from the mount, a force (as described in connection with FIG. 7) is applied to the body. This force widens the opening so the dental component can be freely removed from the mount.

Capture 30 is sized and shaped to engage, hold, and then release a variety of dental components 50. These dental components can be any one of different components manufactured for use in implant dentistry. By way of example, some of these components include, but are not limited to, dental implants, abutments, all types of screws, healing components, collars, cuffs, analogs, surgical drills, and copings. One skilled in the art will appreciate that the present invention may be utilized with other dental components as well.

Figure 11:
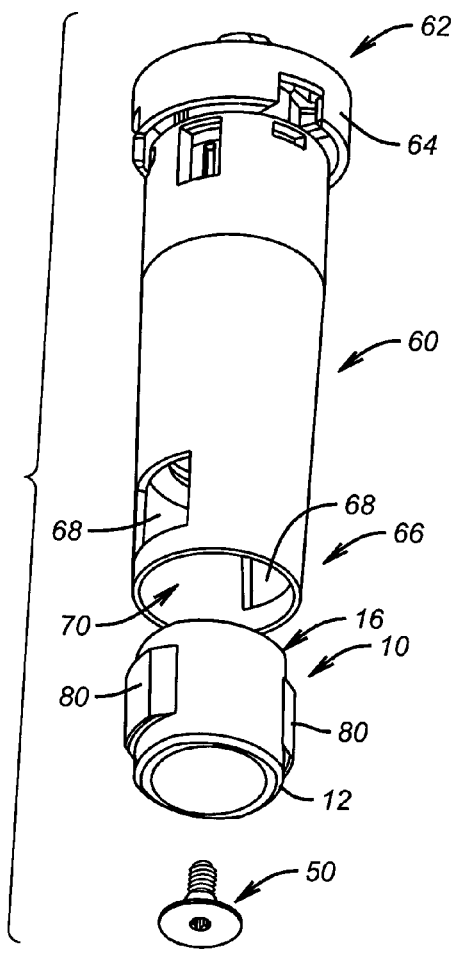
FIG. 11 is an exploded perspective view a mount, a dental screw, and a vial.

Mount 10 of the present invention can be used in a variety of different dental applications. The mount, for example, can be individually package and shipped with an attached dental component. Further, a mount can be provided as part of a larger dental implant system or package. FIG. 11 shows one such example.

FIG. 11 shows a dental component 50, a mount 10, and a vial 60. The vial has an elongated shape with a proximal end 62 having a cap or lid 64 and a distal end 66. The vial includes an internal cavity adapted to house a dental implant and attachment components. The distal end 66 includes two square or rectangular windows 68 that extend into a cylindrical cavity 70 formed in the distal end.

An exterior surface of body 12 includes two square or rectangular projections 80. Mount 10 is sized and shaped to be received in the cavity 70 of vial 60. Specifically, as the distal end 16 of body 12 is positioned into cavity 70, projections 80 engage an inner wall of the cavity until these projections snappingly engage into windows 68. The connection between projections 80 and windows 68 enables the mount to be removeably connected to the vial.

Preferably, the mount is formed from a resilient polymeric material. When the sides of the body are squeezed with a compressive force, the body will deform slightly and then return to its original shape once the force is removed. Alternatively, the mount could be made to "toggle over" when compressed to remain in an open position during the removal of component 50.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A dental mount system, comprising:
   a dental screw; and
   a body forming a recess that is adapted to frictionally engage and hold the dental screw while the body is in a first state, the recess being deformable to a second state different than the first state to release and disengage from the dental screw, the body being deformed from the first state to the second state when a compressive force is applied to an external surface of the body.

2. The mount of claim 1 wherein the recess is shaped as a cylindrical bore.

3. The mount of claim 2 wherein the recess enlarged while in the second state when the compressive force is applied.

4. The mount of claim 3 wherein the recess deforms to a distorted cylindrical bore in the second state.

5. The mount of claim 3 wherein the recess deforms to an elliptical shape in the second state.

6. The mount of claim 1 wherein the recess is formed from two attachment members separated from each other.

7. The mount of claim 6 wherein distal ends of the attachment members are adjacent each other to form the recess.

8. A dental mount system, the system comprising:
a dental component; and
a mount comprising a right circular cylindrical body extending from a proximal end to a distal end and forming an inner cavity, the body including a capture formed in the inner cavity, the capture being adapted to engage and hold the dental component in a first state, the capture being deformable to a second state different than the first state to release and disengage from the dental component when a distortive force is applied to the body.

9. The dental mount system of claim 8 wherein the capture further comprises two attachment members that project inwardly in the inner cavity.

10. The dental mount system of claim 9 wherein the attachment members are oppositely disposed and form an elongated bore adapted to receive the dental component.

11. The dental mount system of claim 10 where each attachment member has a distal end with a hemispherical channel.

12. The dental mount system of claim 11 wherein the channels are adjacent each other to form the elongated bore.

13. The dental mount system of claim 10 wherein the bore deforms as a compressive force is applied to the body.

14. The dental mount system of claim 13 wherein bore has a circular shape in the first state and a distorted circular shape in the second state.

15. The dental mount system of claim 14 wherein the bore has an elliptical shape in the second state.

16. A dental mount system, comprising:
a dental component; and
a body forming a recess that is adapted to frictionally engage and hold the dental component while the body is in a first state, the recess being deformable to a second state different than the first state to release and disengage from the dental component, the body being deformed from the first state to the second state when a compressive force is applied to an external surface of the body.

* * * * *